United States Patent [19]
Sekii et al.

[11] Patent Number: 4,685,470
[45] Date of Patent: Aug. 11, 1987

[54] CARDIAC OUTPUT MEASUREMENT SYSTEM AND METHOD

[75] Inventors: Shigehazu Sekii; Susumu Tanabe, both of Fujinomiya, Japan

[73] Assignee: Terumo Kabushiki Kaisha, Tokyo, Japan

[21] Appl. No.: 799,001

[22] Filed: Nov. 18, 1985

[30] Foreign Application Priority Data

Nov. 21, 1984 [JP]  Japan ................................. 59-244586

[51] Int. Cl.⁴ ................................................. A61B 5/02
[52] U.S. Cl. ...................................... 128/692; 128/713
[58] Field of Search ................ 128/692, 713; 364/716

[56] References Cited

U.S. PATENT DOCUMENTS

| | | | |
|---|---|---|---|
| 3,438,253 | 11/1966 | Kuether et al. | 128/692 |
| 3,595,079 | 7/1971 | Grahn | 128/692 |
| 3,678,922 | 7/1972 | Phillips et al. | 128/692 |
| 3,789,831 | 2/1974 | Kopaniky et al. | 128/692 |
| 3,820,530 | 6/1974 | Gilford et al. | 128/713 |
| 4,004,576 | 1/1977 | Gähwiler et al. | 128/713 |
| 4,035,622 | 7/1977 | Obermajer | 128/713 |
| 4,230,126 | 10/1980 | Elings | 128/692 |
| 4,502,488 | 3/1985 | Degironimo et al. | 128/692 |

Primary Examiner—Lee S. Cohen
Assistant Examiner—David Shay
Attorney, Agent, or Firm—Frishauf, Holtz, Goodman & Woodward

[57] ABSTRACT

An apparatus for measuring cardiac output includes a first system for obtaining cardiac output based on a thermal attenuation method and a second system for obtaining blood flow velocity based on a thermal-type flowrate measurement. A constituent value is obtained from the cardiac output and blood flow velocity, and the constituent value is held. The apparatus also includes a computing unit for computing cardiac output from the already obtained constituent value and a blood flow velocity obtained at the time of measurement. The constituent value can be updated by re-starting the first system.

10 Claims, 6 Drawing Figures

CARDIAC OUTPUT MEASUREMENT SYSTEM AND METHOD

BACKGROUND OF THE INVENTION

1. Field of the Invention:

This invention relates to a cardiac output measurement system used in examining cardiac function.

2. Description of the Prior Art:

In order to measure cardiac output by the right heart catheter method for the purpose of examining cardiac function, the conventional practice is to employ an indicator attenuation method. Let us describe thermal attenuation, which is one of the indicator attenuation methods available, while referring to FIG. 1.

Figure 1:
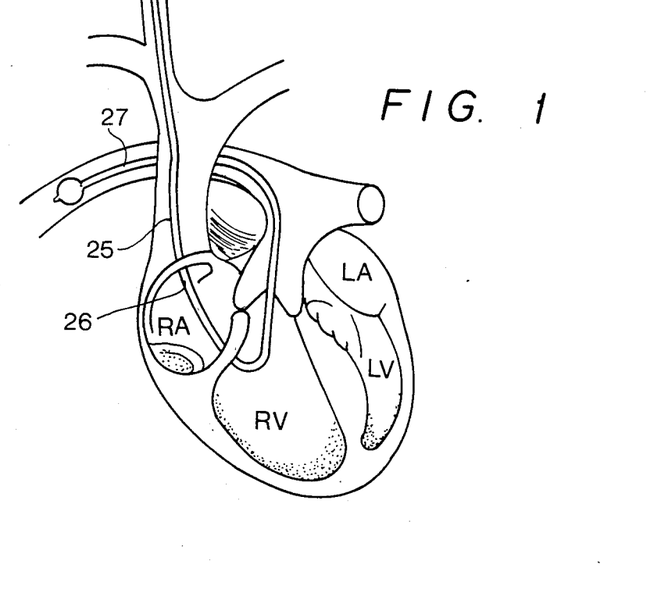
FIG. 1 is a view illustrating a catheter in a position for performing a cardiac output measurement by the thermal attenuation method according to the prior art.
Figure 2:
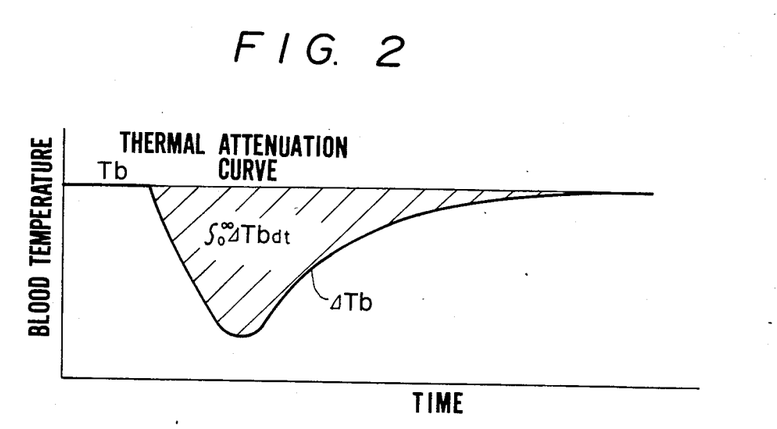
FIG. 2 is a thermal attenuation curve expressing a change in blood temperature due to introduction of a liquid.

According to the right heart catheter method, a catheter 25 is introduced from a pnathic vein, femoral vein or elbow vein and is passed through the superior or inferior vena cava, the right auricle RA and the right ventricle RV to position its distal end in the pulmonary artery. The catheter 25 includes a charge port 26 and a thermistor 27 and is so adapted that the charge port 26 and thermistor 27 occupy positions in the right auricle RA and pulmonary artery, respectively. With the catheter 25 so disposed, a liquid the temperature of which is higher or lower than blood temperature is introduced into the heart from the charge port 26. As the liquid spreads through the right auricle RA and right ventricle RV, the temperature of the liquid is attenuated. The attenuated temperature of the liquid is sensed by the thermistor 27 in the pulmonary artery, allowing cardiac output to be calculated from the area of the attenuation curve (change in temperature with time, as shown in FIG. 2) in accordance with the following Eq. (1), developed by Stewart Hamilton:

$$C.O. = \frac{Si\ Ci\ (Tb - Ti)\ Vi}{Sb\ Cb\ \int_0^\infty \Delta\ Tbdt} \quad (1)$$

where
- C.O: cardiac output,
- Si: specific gravity of injected liquid,
- Ci: specific heat of injected liquid,
- Vi: amount of injected liquid,
- Ti: temperature of injected liquid,
- Tb: temperature of blood,
- Sb: specific gravity of blood,
- Cb: specific heat of blood, $$\int_0^\infty \Delta\ Tbdt:$$

area of attenuation curve

A disadvantage of the conventional cardiac output measurement system which relies upon an indicator attenuation method such as the above-described thermal attenuation method is that measurement of cardiac output is performed intermittently and not continuously. Moreover, when it is attempted to perform measurement frequently, the total amount of injected liquid assumes large proportions, therby submitting the patient to a considerable burden. Another problem is increased risk of infection.

SUMMARY OF THE INVENTION

Accordingly, an object of the invention is to provide a cardiac output measurement system capable of performing a cardiac output measurement continuously with less burden upon the patient and with reduced risk of infection.

According to the present invention, the foregoing object is attained by providing a cardiac output measurement apparatus comprising cardiac output obtaining means for obtaining cardiac output by the thermal attenuation method, blood flow velocity means for obtaining blood flow velocity by a thermal-type flow-rate measurement, means for obtaining a constituent value from the cardiac output and blood flow velocity obtained, means for holding the constituent value obtained, means for starting the blood flow velocity means at every measurement, and calculating means for calculating cardiac output from the constituent value and a newly obtained blood flow velocity each time the blood flow velocity means is started. The apparatus further includes starting means for starting the cardiac output obtaining means, the constituent value being updated whenever the cardiac output obtaining means is started.

In another aspect of the invention, the cardiac output measurement apparatus comprises a catheter-type sensor having a liquid charging section and internally accommodating a first temperature-sensitive element for sensing blood temperature attenuated by a liquid and a second temperature-sensitive element heated by heating means; first temperature detecting means for detecting a signal indicative of blood temperature sensed by the first temperature-sensitive element; thermal attenuation-type cardiac output calculating means for calculating cardiac output based on the thermal attenuation method using a signal from the first temperature detecting means; second temperature detecting means for detecting the temperature of the heated second temperature-sensitive element; blood flow velocity calculating means for calculating blood flow velocity based on a signal from the second temperature detecting means and a signal from the first temperature detecting means; holding means for calculating, and for holding as a calibration value, a blood vessel cross-sectional area based on the cardiac output calculated by the thermal attenuation-type cardiac output calculating means and the blood flow velocity calculated by the blood flow velocity calculating means; and cardiac output calculating means for calculating cardiac output based on the calibration value from the holding means and the blood flow velocity.

In an embodiment of the present invention, the second temperature-sensitive element comprises a self-heating thermistor. The thermal attenuation-type cardiac output calculating means is adapted to calculate cardiac output from an amount of injected liquid, temperature of the injected liquid, specific gravity of the injected liquid, specific heat of the injected liquid, blood temperature, specific gravity of the blood and an integrated value of a thermal attenuation curve.

According to an embodiment of the invention, the blood flow velocity calculating means comprises means for calculating blood flow velocity from a fixed current value, blood temperature, temperature and resistance value or potential difference of the heated self-heating thermistor.

The holding means comprises arithmetic means for comparing and calculating blood vessel cross-sectional area from the cardiac output value based on the thermal attenuation method and the blood flow velocity value, and sample-and-hold means for holding a value calculated by the arithmetic means.

The present invention also provides a cardiac output measurement method comprising a first step of obtaining cardiac output by the thermal attenuation method, a second step of obtaining blood flow velocity by a thermal-type flowrate measurement, third step of obtaining a constituent value from the cardiac output and blood flow velocity, a fourth step of obtaining blood flow velocity at continuous measurement instants, and a fifth step of obtaining cardiac output from the blood flow velocity obtained and the constituent value. The cardiac output measurement method further includes a step of re-starting the first step and updating the constituent value.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Figure 3:
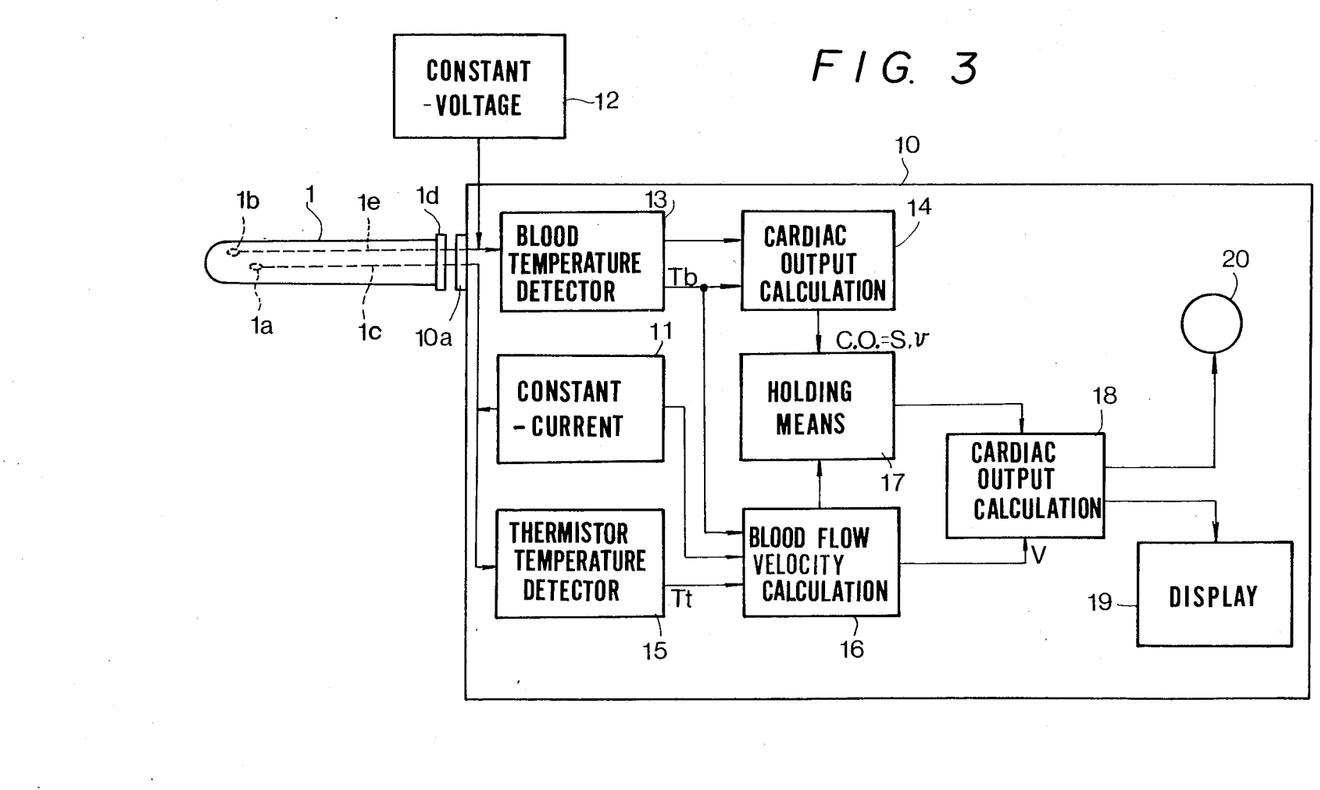
FIG. 3 is a block diagram illustrating an embodiment of a cardiac output measurement apparatus according to the present invention.

Turning now to the drawings and referring first particularly to FIG. 3, a cardiac output measurement apparatus embodying the present invention includes a catheter-type sensor 1 comprising a first temperature-sensitive element 1a constituted by means such as a self-heating thermistor or the like, a second temperature-sensitive element 1b constituted by a thermistor or thermocouple, a connecter 1d, and lead wires 1c, 1e interconnecting the first and second temperature-sensitive elements 1a, 1b with the connector 1d, respectively. The catheter-type sensor 1 having this construction is introduced into the pulmonary artery by the right heart catheter method through a conventional technique similar to that described above. The apparatus further comprises a cardiac output measuring unit 10 including a constant-current circuit 11, first temperature detecting means 13 for detecting blood temperature, cardiac output calculating means 14 for calculating cardiac output based on the thermal attenuation method, second temperature detecting means 15 for detecting the temperature of a heated thermistor, blood flow velocity calculating means 16, holding means 17, cardiac output calculating means 18, display means 19 and a recorder output terminal 20. A constant-voltage circuit 12 drives the second temperature-sensitive element 1b connected to the measurement unit 10.

The second temperature-sensitive element 1b accommodated internally of the catheter-type sensor 1 is for sensing blood temperature in the pulmonary artery. The first temperature-sensitive element 1a, which is also housed within the sensor 1, is heated by a constant current supplied by the constant current circuit 11 and is for sensing its own temperature. The first temperature-sensitive element 1a is preferably constituted by a self-heating type thermistor but is not limited thereto, for any temperature-sensitive element such as an ordinary thermistor heated by heating means which produces a constant amount of heat may be used. The self-heating thermistor is preferred structurally because it is easy to incorporate and functionally because of its stable heat generating and sensing properties.

The second temperature-sensitive element 1b is connected to the constant-voltage circuit 12 and blood temperature detecting means 13 via the lead wire 1e, connector 1d and a connector 10a, which constitutes part of the measuring unit 10. A signal produced by the second temperature-sensitive element 1b indicative of pulmonary artery blood temperature is applied to the blood temperature detecting means 13 where the signal is detected and delivered in a form suitable for signal processing.

The blood temperature detecting means 13 is connected to the cardiac output calculating means 14 for applying an output blood temperature signal thereto. Using Eq. (1), the calculating means 14 calculates cardiac output from the area of the attenuation curve of FIG. 2 by the thermal attenuation method in accordance with the Hamilton process.

The first temperature-sensitive element 1a in sensor 1 is connected to the heated thermistor temperature detecting means 15 and constant-current circuit 11 via the lead wire 1c and connectors 1d, 10a. When necessary, the constant-current circuit 11 supplies the first temperature-sensitive element 1a with a prescribed current to heat the same. A signal produced by the first temperature-sensitive element 1a indicative of the heating temperature is applied to the thermistor temperature detecting means 15. Here a signal is a potential difference detected as the heated thermistor resistance value and temperature signal of the first temperature-dependent element 1a. The output of the detecting means 15 is used for calculating blood flow velocity. The heated thermistor detecting means 15 and the blood temperature detecting means 13 are connected to the blood flow velocity calculating means 16 which, based on the inputs thereto, calculates the velocity of blood flow.

Let us now describe the principle and method of calculating blood flow velocity as performed by the blood flow velocity calculating means 16. Let Rt represent the resistance value of the thermistor constituting the first temperature-sensitive element 1a, and let Ic denote the magnitude of the current applied to this thermistor by the constant-current circuit 11. When the thermistor of the first heat-sensitive element 1a is heated, the quantity of heat generated per unit time will be $Ic^2 \cdot Rt$.

When the heated thermistor of the first heat-sensitive element 1a is placed in blood flowing at a velocity v, the thermistor is cooled to an extent dependent upon the blood flow velocity v. The quantity of heat lost by such cooling is expressed by $K \cdot v \cdot (Tt-Tb)$, where Tb is the blood temperature, Tt is the temperature of the heated thermistor, and K is a constant of proportion. The temperature of the thermistor constituting the first temperature-sensitive element 1a is maintained at a temperature which will establish equivalence between the quantity of heat generated and the quantity of heat taken away by cooling. Expressing the foregoing by an equation, we have $$Ic^2 \cdot Rt = K \cdot v \cdot (Tt - Tb) \tag{2}$$

The following equation for finding blood flow velocity is derived from Eq. (2):

$$v = (1/K)(Ic^2 \cdot Rt)/(Tt - Tb) \tag{3}$$

Since the heated thermistor is driven by the constant-current circuit 11, the potential difference across the ends of the heated thermistor lead wire 1c may be detected as an alternative to detecting the resistance value Rt. In such case the potential difference, denoted Vo, is equal to Rt·Ic, so that Eq. (3) may be rewritten as follows:

$$V = (1/K) \, Ic \cdot Vo)/(Tt - Tb) \tag{3'}$$

It will be obvious from Eq. (3) or (3') that the blood flow velocity may be obtained from the resistance value Rt, or the potential difference Vo, of the heated thermistor, taken together with the temperature Tt of the heated thermistor of the first temperature-sensitive element 1a, the blood temperature Tb, constant-current value Ic and constant K. The heated thermistor temperature detecting means 15 provides the blood flow velocity calculating circuit 16 with the resistance value Rt or potential difference Vo of the heated thermistor of first temperature-sensitive element 1a, and with temperature Tt of this thermistor. The blood temperature detecting means 13 applies the blood temperature Tb to the blood flow velocity detecting means 16. The latter calculates the blood flow velocity v in accordance with Eq. (3) or (3') based on the information received.

Note that though the constant-current value Ic can be obtained by detecting the current of the constant-current circuit 11, it is also possible to provide the blood flow velocity calculating means 16 with Ic in the form of a constant term, as in the manner of the constant of proportion K.

The blood flow velocity calculating means 16 and the thermal attenuation-type cardiac output measuring means 14 are connected to the holding means 17. The holding means 17 comprises arithmetic means for calculating blood vessel cross-sectional area, and sample-and-hold means for holding the blood vessel cross-sectional area value calculated by the arithmetic means. The holding means 17 also functions to compare the cardiac output value, calculated by means 14 in accordance with the thermal attenuation method, and the blood flow velocity value obtained from the blood flow velocity calculating means 16.

Let S represent the blood vessel cross-sectional area of the pulmonary artery. The cardiac output value C.O. and blood flow velocity value v are related as follows:

$$C.O. = S \cdot v \tag{4}$$

The holding means 17 compares the cardiac output value C.O. and the blood flow velocity value v, finds the blood vessel cross-sectional area S in accordance with Eq. (4) and holds the value S as a calibration value.

The following equation may be derived from Eqs. (3) and (4):

$$C.O. = (S/K) \cdot (Ic^2 \cdot Rt)/(Tt - Tb) \tag{5}$$

$$= (S/K) \cdot (Ic \cdot Vo)/(Tt - Tb)$$

in which S/K can be held as the calibration value.

The holding means 17 and blood flow velocity calculating means 16 are connected to the cardiac output calculating means 18. The latter makes it possible to obtain a continuous cardiac output value by multiplying the blood flow velocity, which is measured continuously by the blood flow velocity calculating means 16, by the calibration value held in the holding means 17. The cardiac output calculating means 18 is connected to the display means 19 and recorder output terminal 20 so that the cardiac output obtained may be continuously displayed and recorded.

The blood vessel cross-sectional area S varies with time; hence, even though S is held as a calibration value, the change in S can make it difficult to obtain an accurate cardiac output. To overcome this problem, cardiac output is measured by the cardiac output calculating means 14 in accordance with the thermal attenuation method, a new value of the blood vessel cross-sectional area S is obtained by the holding means 17 in accordance with Eq. (4), and this is held as the calibration value.

The thermal attenuation-type cardiac output calculating means 14, heated thermistor detecting means 15, blood flow velocity calculating means 16, holding means 17 and cardiac output calculating means 18 may be advantageously constituted by a microcomputer comprising a one-chip LSI. In such case, the entire control sequence would be stored in an internal memory. In addition, the blood temperature detecting means 13 and heated thermistor temperature detecting means 15 would both be realized by analog-digital converters and these would also be incorporated in the one-chip microcomputer.

Figure 4:
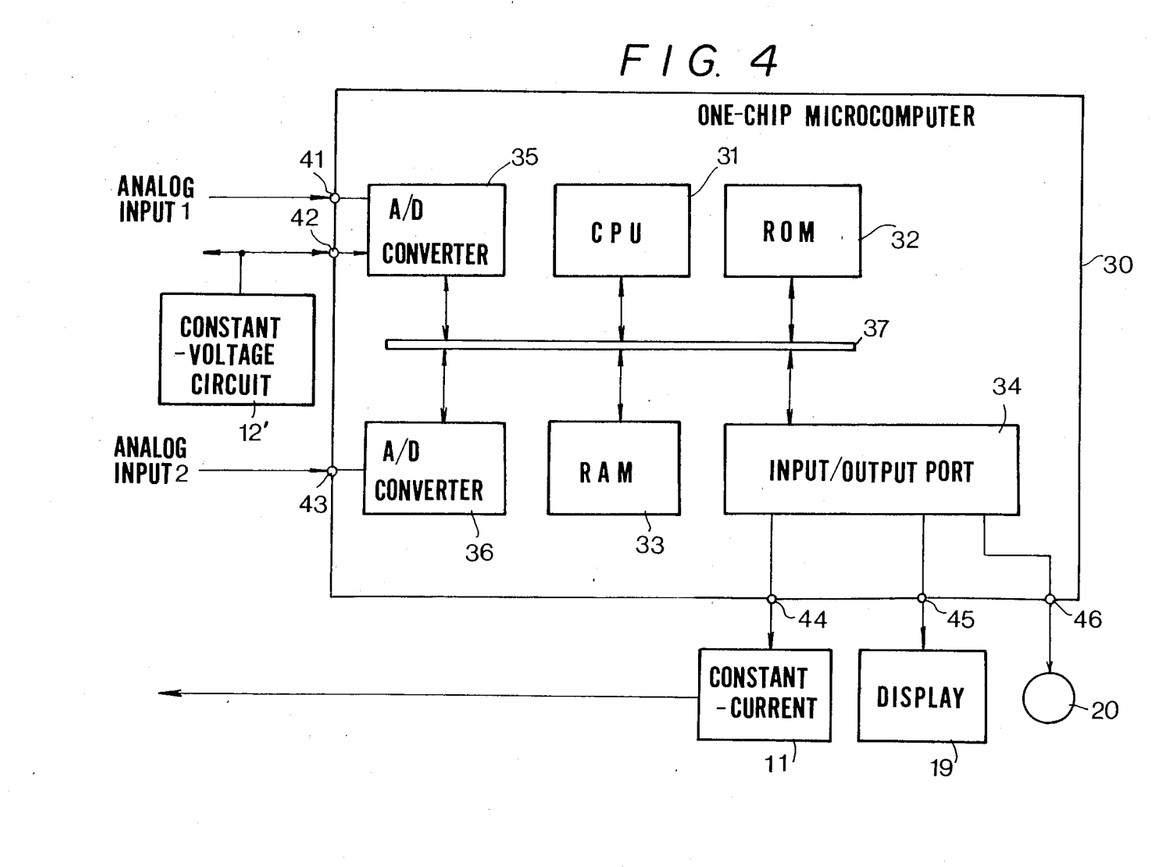
FIG. 4 is a view showing the arrangment of a one-chip microcomputer according to an embodiment of the present invention.

FIG. 4 is a block diagram of a one-chip microcomputer for executing the above-described functions. A CPU 31 executes various processing in accordance with a program stored in a ROM 32. The results of processing are stored in a RAM 33. An input/output port 34 includes an output port 44 for controlling the ON/OFF operation of the constant-current circuit 11, and output port 45 for controlling the display of information on the display means 19, and an output port 46 connected to the output terminal 20. An analog-digital converter 35 corresponds to the blood temperature detecting means 13, and an analog-digital converter 36 corresponds to the heated thermistor temperature detecting means 15. These converters 35, 36 receive analog signals at respective analog input terminals 41, 43 and convert these signals into digital signals for processing by the CPU 31.

Figure 5:
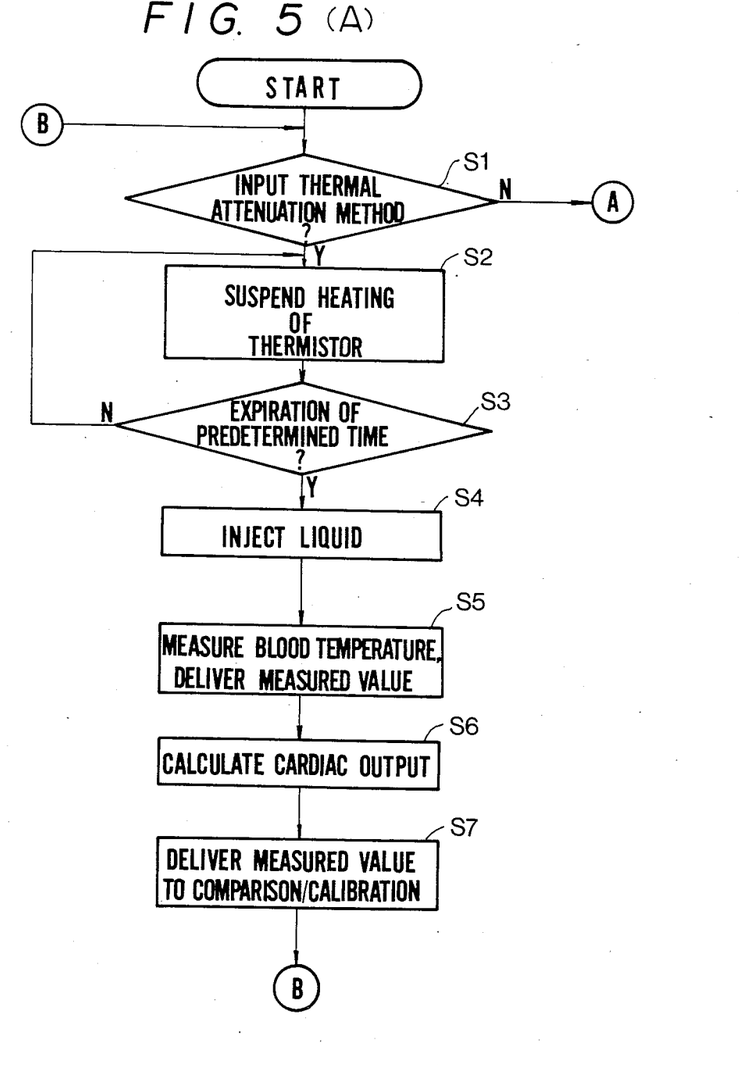
FIGS. 5(A) and 5(B) are flowcharts illustrating the operation of a cardiac output measurement apparatus embodying the present invention.

The sections 13 through 18 in FIG. 3 represent, in block form, the functions implemented by the above-described microcomputer. Let us now turn to the flowcharts of FIGS. 5(A) and 5(B0 to describe the details of a control sequence which the CPU 31 executes in accordance with a processing program stored in ROM 32. This will serve as a specific example of a cardic output measurement operation performed by the cardiac output measurement apparatus embodying the present invention.

The first step S1 is a monitoring step to determine whether or not there is an indication of a cardiac output measurement in accordance with the thermal attenuation method. When there is such an indication, the program advances to a step S2, where heating of the thermistor constituting the first temperature-sensitive element 1a is suspended. Next, a step S3 calls for waiting for the passage of a predetermined period of time until the thermistor of first temperature-sensitive element 1a is no longer influenced by heating. When this is achieved at passage of the predetermined time period, a step S4 calls for injecting a prescribed amount of a diluting liquid from a charge port, not shown, similar in structure to the charge port 26 of the catheter-type sensor 1 shown in FIG. 1. The blood temperature detecting means 13 measures the temperature Tb of the diluted blood at a step S5 and delivers a signal indicative of the measured value to the thermal attentuation-type cardiac output calculating means 14. Upon receiving the signal, the calculating means 14 calculates the cardiac output C.O. in accordance with Eq. (1). This is step S6 of the flowchart. Next, at a step S7, the calculated value of cardiac output is delivered to the holding means 17. Since this ends measurement of the cardiac output C.O. in accordance with the thermal-attenuation method, the program returns to the step S1.

Figure 5B:
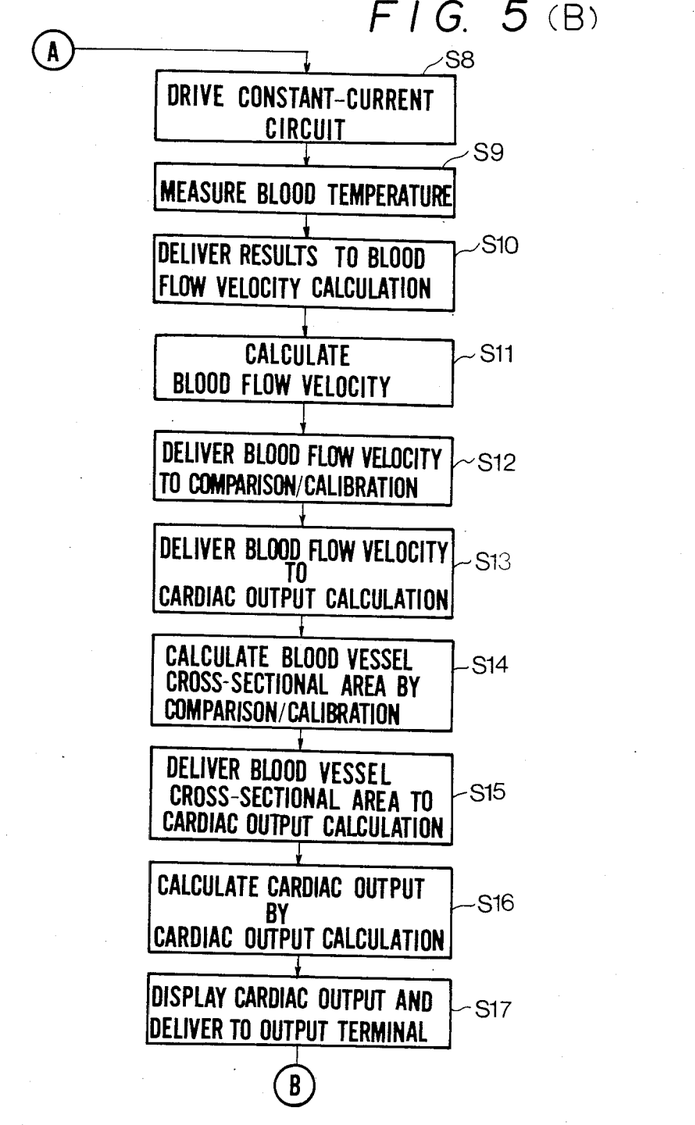

If there is no indication of measured cardiac output in accordance with the thermal-attenuation method at step S1, then the program shifts to a step S8, at which the constant-current circuit 11 is driven into operation to heat the thermistor of first temperature-sensitive element 1a by supplying it with a predetermined current Ic. This is followed by a step S9, at which the heated temperature detecting means 15 detects the temperature Tt of the heated thermistor proper, as well as the resistance value Rt or potential different Vo thereof. These values are delivered to the blood flow velocity calculating means 16 at a step S10. Next, at a step S11, the blood flow velocity calculating means 16 calculates the blood flow velocity v in accordance with Eq. (3) or (3') upon receiving the temperature Tt and resistance value Rt or potential difference Vo from the temperature detecting means 15, and the blood temperature Tb from the blood temperature detecting means 13. The value of the calculated blood flow velocity v is delivered to the holding means 17 at a step S12 and to the cardiac output calculating means 18 at a step S13.

This is followed by a step S14, at which the holding means 17 obtains, and holds as a calibration value, the blood vessel cross-sectional area S in accordance with Eq. (4) by using the cardiac output C.O. from the thermal attenuation-type cardiac output calculating means 14 and the blood blow velocity v. This value is delivered to the cardiac output calculating means 18 at a step S15. The next step S16 calls for the cardiac output calculating means 18 to obtain the cardiac output C.O., associated with the first temperature-dependent element 1a, from the blood flow velocity v and the calibration value from the holding means 17. The value of the cardiac output obtained is displayed by the display means 19 and, when necessary, delivered to the output terminal 20 at a step S17. This ends one cycle of a continuous cardiac output measurement, with the program returning to the step S1. Continuous measurement of cardiac output is performed by executing the processing from step S8 to step S17 until an indication of cardiac output measurement based on the thermal attenuation method is again obtained.

ADVANTAGES OF THE INVENTION

The cardiac output measurement apparatus of the present invention makes it possible to measure cardiac output in a continuous manner. This is accomplished by adopting a thermal-type flowrate measurement method in which a thermistor or the like is heated. Thus, the invention does not rely upon an intermittent method of the type in which cardiac output is measured by an indicator attenuation method, such as the thermal attenuation method.

With the thermal attenuation method, the patient is subjected to a significant burden by injecting of the liquid when measurements are frequent. According to the apparatus of the present invention, however, measurement can be performed continuously by a minimum of one liquid charge, thereby lightening the burden upon the patient, simplifying operation and reducing the risk of infection.

According to the present invention, blood flow velocity is measured at the same time as cardiac output, and blood vessel cross-sectional area is calculated and held. Therefore, if the blood vessel is assumed to have a circular cross section, blood vessel diameter can be readily calculated from the following equation:

$$S = \pi (l/2)^2 \qquad (6)$$

where
S: blood vessel cross-sectional area
l: blood vessel diameter

This makes it possible to obtain knowledge relating to blood flow velocity, blood vessel cross-sectional area and blood vessel diameter. Such knowledge is important in terms of examining cardiac function.

As many apparently widely different embodiments of the present invention can be made without departing from the spirit and scope thereof, it is to be understood that the invention is not limited to the specific embodiments thereof except as defined in the appended claims.

What we claim is:

1. A cardiac output measurement apparatus, comprising:
   cardiac output obtaining means for obtaining cardiac output by a thermal attenuation method;
   blood flow velocity means for obtaining blood flow velocity by a thermal-type flowrate measurement;
   means for obtaining a constituent value functionally related to the cardiac output and blood flow velocity obtained by said cardiac output obtaining means and said blood flow velocity means;
   storing means for holding the constituent value obtained;
   means for starting said blood flow velocity means during continuous measurement instants;
   means for updating said constituent value including means for initiating said cardiac output obtaining means to measure a new cardiac output; and
   calculating means for calculating cardiac output from the constituent value held in said storing means and as updated by said updating means, and a newly obtained blood flow velocity each time said blood flow velocity means is started.

2. The apparatus according to claim 1, further comprising restarting means for restarting said cardiac output obtaining means, the constituent value being updated whenever said cardiac output obtaining means is restarted.

3. A cardiac output measurement apparatus comprising:
- a catheter-type sensor having a liquid charging section and internally accommodating a first temperature-sensitive element for sensing blood temperature attenuated by a liquid and a heated second temperature-sensitive element;
- first temperature detecting means for detecting a signal indicative of blood temperature sensed by said first temperature-sensitive element;
- thermal attenuation-type cardiac output calculating means for calculating cardiac output based on a thermal attenuation method using an output signal from said first temperature detecting means;
- second temperature detecting means for detecting a temperature of the heated second temperature-sensitive element;
- blood flow velocity calculating means for calculating blood flow velocity based on an output signal from said second temperature detecting means and an output signal from said first temperature detecting means;
- holding means for calculating, and for holding as a calibration value, a blood vessel cross-sectional area based on the cardiac output calculated by said thermal attenuation-type cardiac output calculating means and the blood flow velocity calculated by said blood flow velocity calculating means; and
- cardiac output calculating means for calculating cardiac output based on the calibration value from said holding means and the blood flow velocity.

4. The apparatus according to claim 3, wherein said second temperature-sensitive element comprises a self-heating thermistor.

5. The apparatus according to claim 3, wherein said thermal attenuation-type cardiac output calculating means calculates cardiac output from an amount of injected liquid, temperature of the injected liquid, specific gravity of the injected liquid, specific heat of the injected liquid, blood temperature, specific gravity of the blood and a value obtained by integrating a thermal attenuation curve.

6. The apparatus according to claim 3, wherein said holding means comprises arithmetic means for comparing and calculating blood vessel cross-sectional area from the cardiac output value based on the thermal attenuation method and the blood flow velocity value, and sample-and-hold means for holding a value calculated by said arithmetic means.

7. The apparatus according to claim 4, wherein said blood flow velocity calculating means comprises means for calculating blood flow velocity from a constant-current value, blood temperature, and temperature and resistance value of said heated self-heating thermistor.

8. The apparatus according to claim 4, wherein said blood flow velocity calculating means comprises means for calculating blood flow velocity from a constant-current value, blood temperature, and the temperature of and potential difference developed by said heated self-heating thermistor.

9. A cardiac output measurement method, comprising:
- a first step of obtaining cardiac output by a thermal attenuation method;
- a second step of obtaining blood flow velocity by a thermal-type flowrate measurement;
- a third step of obtaining a constituent value functionally related to the obtained cardiac output and blood flow velocity;
- a fourth step of obtaining blood flow velocity at continuous measurement instants;
- a fifth step of updating the constituent value by initiating said first step thereby obtaining a new cardiac output; and
- a sixth step of obtaining cardiac output from the blood flow velocity obtained and the already obtained constituent value as updated in said fifth step.

10. The method according to claim 9, further comprising a step of re-starting said first step and updating the constituent value.

* * * * *

UNITED STATES PATENT AND TRADEMARK OFFICE
CERTIFICATE OF CORRECTION

PATENT NO. : 4,685,470
DATED : August 11, 1987
INVENTOR(S) : SEKII et al

It is certified that error appears in the above-identified patent and that said Letters Patent is hereby corrected as shown below:

Column 5, line 22, "v=1/K) (Ilc Vo)..." should be --v=(1/K) (Ic.Vo)--.

Claim 8, column 10, line 19, "a" should be inserted after "and".

Signed and Sealed this

Sixteenth Day of February, 1988

*Attest:*

*Attesting Officer*

DONALD J. QUIGG

*Commissioner of Patents and Trademarks*